United States Patent
Vercellotti et al.

(10) Patent No.: US 8,808,295 B2
(45) Date of Patent: *Aug. 19, 2014

(54) INSERT FOR A HANDHELD ULTRASOUND SURGICAL DEVICE

(76) Inventors: Tomaso Vercellotti, Genoa (IT);
Domenico Vercellotti, Genoa (IT);
Fernando Bianchetti, Genoa (IT)

(*) Notice: Subject to any disclaimer, the term of this patent is extended or adjusted under 35 U.S.C. 154(b) by 565 days.

This patent is subject to a terminal disclaimer.

(21) Appl. No.: 12/364,720

(22) Filed: Feb. 3, 2009

(65) Prior Publication Data

US 2009/0136894 A1 May 28, 2009

Related U.S. Application Data

(63) Continuation of application No. 11/396,593, filed on Apr. 4, 2006.

(30) Foreign Application Priority Data

Jun. 21, 2005 (IT) .............................. MI2005A1172

(51) Int. Cl.
*A61B 17/32* (2006.01)
(52) U.S. Cl.
USPC .............................................. 606/79; 606/169
(58) Field of Classification Search
USPC ..................... 606/79–85, 159, 167–170, 180;
30/123.3; 408/57, 59, 211, 212;
604/19, 22; 433/86, 119, 165
See application file for complete search history.

(56) References Cited

U.S. PATENT DOCUMENTS

| | | | |
|---|---|---|---|
| 2,984,241 A | 5/1961 | Carlson |
| 4,188,952 A | 2/1980 | Loschilov et al. |
| 4,248,232 A | 2/1981 | Engelbrecht et al. |
| 4,473,075 A | 9/1984 | Rexroth |
| 4,702,697 A | 10/1987 | Linkow |
| 4,832,683 A | 5/1989 | Idemoto et al. |
| 5,026,387 A | 6/1991 | Thomas |
| 5,115,813 A | 5/1992 | Ylander et al. |
| 5,122,134 A | 6/1992 | Borzone et al. |
| 5,123,841 A | 6/1992 | Millner |
| 5,195,960 A | 3/1993 | Hossain et al. |

(Continued)

FOREIGN PATENT DOCUMENTS

| | | |
|---|---|---|
| EP | 0238667 A1 | 9/1987 |
| EP | 0456470 A1 | 11/1991 |
| WO | 87/05793 A1 | 10/1987 |

OTHER PUBLICATIONS

Non-Final Office Action dated Nov. 9, 2009, United States Patent & Trademark Office, U.S. Appl. No. 11/396,593, filed Apr. 4, 2006.

(Continued)

*Primary Examiner* — Eduardo C. Robert
*Assistant Examiner* — Julianna N Harvey
(74) *Attorney, Agent, or Firm* — Vierra Magen Marcus LLP

(57) ABSTRACT

An insert for a handheld ultrasound surgical device is disclosed. The insert comprises an interface to receive ultrasound vibrations and provide fluid to a channel within the insert. The insert also comprises a tip having a plurality of cutting elements disposed in a substantially circular configuration. Each of the cutting elements is disposed radially from the opening to provide a plurality of corridors that allows that fluid to pass from the opening to an edge of the tip.

18 Claims, 10 Drawing Sheets

(56) References Cited

U.S. PATENT DOCUMENTS

| | | | |
|---|---|---|---|
| 5,318,570 A * | 6/1994 | Hood et al. .................... | 606/169 |
| 5,342,380 A | 8/1994 | Hood | |
| 5,643,304 A | 7/1997 | Schechter et al. | |
| 5,752,924 A | 5/1998 | Kaufman et al. | |
| 5,776,092 A | 7/1998 | Farin et al. | |
| 5,843,109 A | 12/1998 | Mehta et al. | |
| 5,922,003 A | 7/1999 | Anctil et al. | |
| 5,935,143 A | 8/1999 | Hood | |
| 5,968,007 A | 10/1999 | Simon et al. | |
| 5,997,298 A | 12/1999 | Nowak | |
| 6,017,354 A | 1/2000 | Culp et al. | |
| 6,117,152 A | 9/2000 | Huitema | |
| 6,149,434 A | 11/2000 | Gault | |
| 6,257,889 B1 * | 7/2001 | Boston .......................... | 433/165 |
| 6,267,592 B1 * | 7/2001 | Mays ............................ | 433/165 |
| 6,267,594 B1 | 7/2001 | Hugo | |
| 6,695,847 B2 * | 2/2004 | Bianchetti et al. .............. | 606/79 |
| 6,818,001 B2 * | 11/2004 | Wulfman et al. .............. | 606/170 |
| 2004/0030254 A1 * | 2/2004 | Babaev ........................ | 600/459 |
| 2005/0064368 A1 * | 3/2005 | Kitamura et al. ............. | 433/165 |

OTHER PUBLICATIONS

Non-Final Office Action, United States Patent & Trademark Office, U.S. Appl. No. 10/716,437, filed Nov. 20, 2003, Nov. 29, 2007.

Response to Non-Final Office Action, U.S. Appl. No. 10/716,437, filed Nov. 20, 2003, Apr. 24, 2008.

Final Office Action, United States Patent & Trademark Office, U.S. Appl. No. 10/716,437, filed Nov. 20, 2003, Jul. 22, 2008.

Non-Final Office Action, United States Patent & Trademark Office, U.S. Appl. No. 11/396,593, filed Apr. 4, 2006, Sep. 25, 2008.

Response to Final Office Action, U.S. Appl. No. 10/716,437, filed Nov. 20, 2003, Sep. 30, 2008.

Response to Non-Final Office Action, U.S. Appl. No. 11/396,593, filed Apr. 4, 2006, Feb. 2, 2009.

Final Office Action dated Apr. 22, 2009, United States Patent & Trademark Office, U.S. Appl. No. 11/396,593, filed Apr. 4, 2006.

Response to Final Office Action dated Jun. 22, 2009, U.S. Appl. No. 11/396,593, filed Apr. 4, 2006.

Amendment Under 37 CFR 1.114 Submitted With RCE dated Aug. 24, 2009, U.S. Appl. No. 11/396,593, filed Apr. 4, 2006.

Final Office Action dated May 10, 2010, United States Patent & Trademark Office, U.S. Appl. No. 11/396,593, filed Apr. 4, 2006.

Response to Non-Final Office Action dated Feb. 3, 2010, U.S. Appl. No. 11/396,593, filed Apr. 4, 2006.

Response to Non-Final Office Action mailed Jan. 3, 2011, U.S. Appl. No. 11/954,676, filed Dec. 12, 2007.

Notice of Allowance and Fee(s) Due dated Jan. 26, 2011, U.S. Appl. No. 11/396,593, filed Apr. 4, 2006.

Non-Final Office Action dated Sep. 16, 2010, U.S. Appl. No. 11/954,676, filed Dec. 12, 2007.

Notice of Allowance and Fee(s) Due dated Apr. 14, 2011, U.S. Appl. No. 11/954,676, filed Dec. 12, 2007.

* cited by examiner

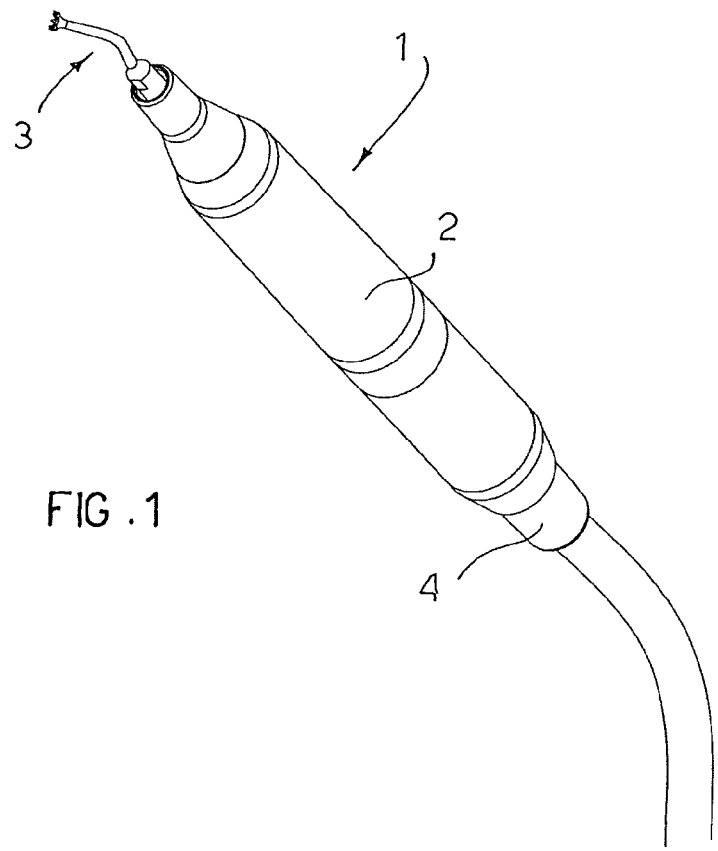
FIG. 1
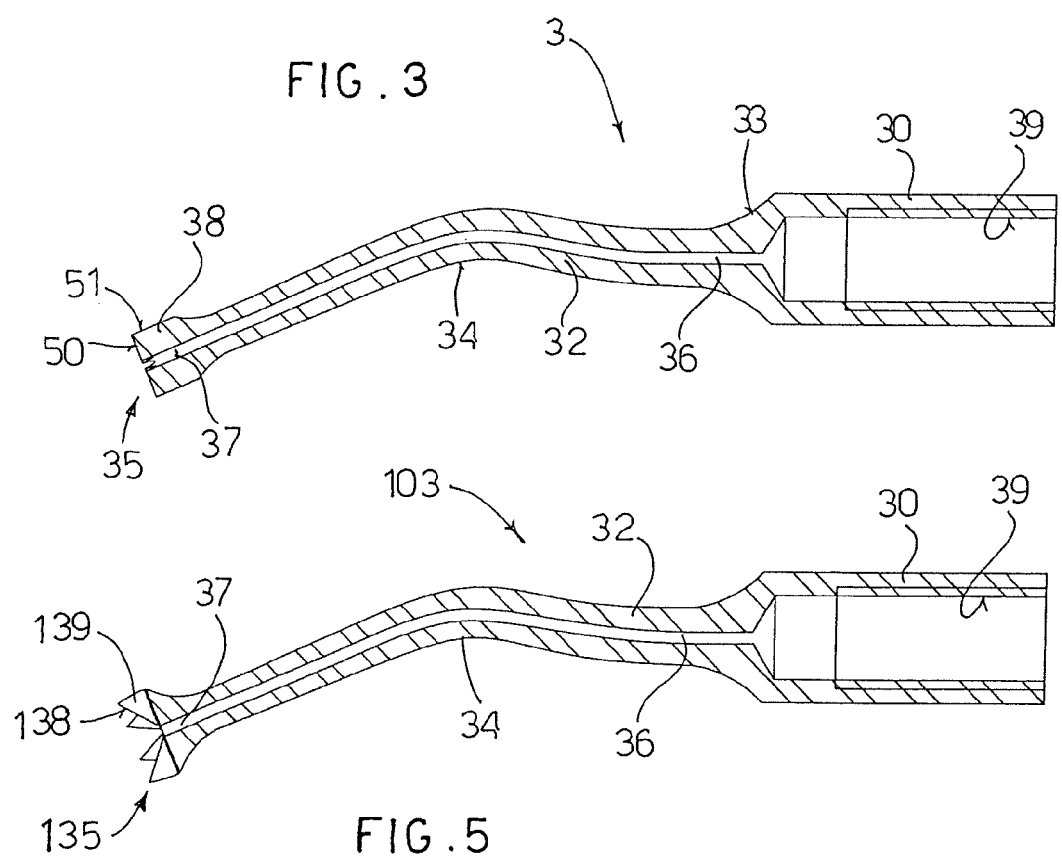
FIG. 3
FIG. 5

INSERT FOR A HANDHELD ULTRASOUND SURGICAL DEVICE

CROSS-REFERENCE TO RELATED APPLICATIONS

This application is a continuation of U.S. patent application Ser. No. 11/396,593 filed on Apr. 4, 2006 (still pending); which claims priority to Italian Patent Application Serial No. MI2005A 001172 filed on Jun. 21, 2005.

FIELD OF THE INVENTION

The present invention refers to a surgical method of implant site preparation, in particular for endosseous dental implantology and to a piezoelectric surgical device used to implement said method.

BACKGROUND OF THE INVENTION

Endosseous dental implantology uses cylindrical or conical implants which are inserted into a hole made in the bone called the implant site. The implant site is generally made with spiral-shaped rotating drills, driven by micromotors. The drills have variable diameters and are applied in ascending order until a hole of the size chosen to accommodate the implant is obtained.

These methods present severe limitations if they are to be used in difficult situations (such as, for example, restricted surgery access or anatomically delicate bone conditions, and in particular when it is necessary to operate in the vicinity of soft tissue.

The cutting characteristics of the techniques currently in use are unsatisfactory because the rotation of the drill and the consequent macrovibrations generated reduce the operator's tactile sensitivity with a consequent loss of control of the cutting depth. Furthermore, the high mechanical energy produced by the use of these instruments increases the risk of overheating of the tissues involved, compromising healing thereof.

Rotating drills act both on mineralized and non-mineralized tissue and consequently it is possible to damage involuntarily the soft tissue and the delicate structures (for example the vascular nerve bundles) near to the operating field.

SUMMARY OF THE INVENTION

The object of the invention is to overcome the drawbacks of the prior art through the use of a surgical device combined with a method for preparation of the implant site which allow surgical procedures to be performed with extreme precision and control, maximum intra-operative visibility and selectivity of cutting, with an increase in safety and a reduction in the above described risks.

These objects are achieved in accordance with the invention with the characteristics listed in appended independent claims 1 and 3.

Preferred embodiments of the invention will be apparent from the dependent claims.

The surgical device for implant site preparation according to the invention comprises:
 a body designed to be gripped by the user;
 an insert mounted on the head of said body and having such a shape as to be able to operate on bone tissues, and
 an ultrasonic transducer disposed inside the body and connected to said insert to make it vibrate at a frequency in the ultrasound range.

The insert comprises a tip consisting of a plurality of cutting elements disposed in a substantially circular configuration. In the body of the insert there is provided a channel which ends in an outlet channel opening in the tip of the insert for passage of an irrigating fluid, so as to cool efficiently the work area involved by the tip of the insert and at the same time to exploit the physical effect of cavitation which allows a greater cleaning of the operating field with a consequent increase in visibility with respect to the conventional method.

The object of this patent is the preparation of the implant site for cylindrical or conical implants using a suitable ultrasonic instrument for bone surgery, such as that described in U.S. Pat. No. 6,695,847, with specially designed inserts provided with internal irrigation means.

The combined use of the ultrasonic device and of the aforementioned insert allows an implant site to be made with great surgical ease and with an excellent tissue response, with an acceleration of the mechanisms of healing and of new bone formation, as shown by tests and experimental research in animals (as reported below).

BRIEF DESCRIPTION OF THE DRAWINGS

Further characteristics of the invention will be made clearer by the detailed description that follows, referring to a purely exemplary and therefore non-limiting embodiment thereof, illustrated in the appended drawings, in which:

FIG. 1 is a perspective view illustrating an ultrasound handpiece according to the invention;

FIG. 3 is a sectional view of the insert of FIG. 2;

FIG. 5 is a sectional view of the insert of FIG. 4;

DETAILED DESCRIPTION OF THE INVENTION

Figure 2:
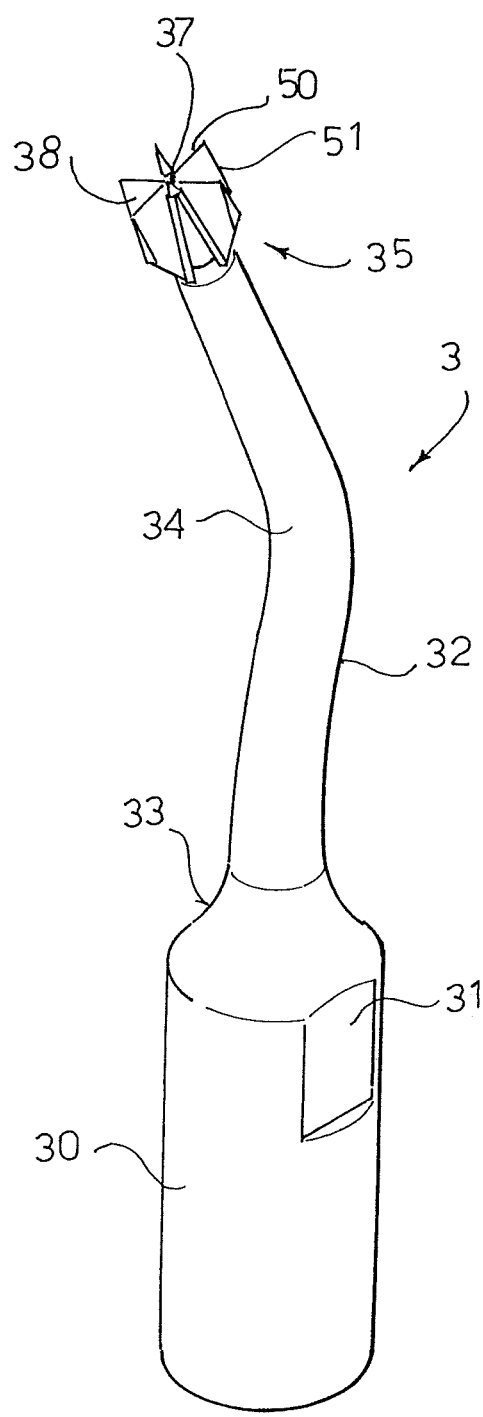
FIG. 2 is a perspective view of the insert mounted on the handpiece of FIG. 1.

A surgical device according to the invention, which is denoted as a whole with a reference numeral 1, is described with the aid of the figures. As shown in FIG. 1, the surgical device 1 is a handpiece that comprises a body 2, substantially cylindrical in shape so that it can be easily gripped by a surgeon. At the head of the body 2 is mounted an insert 3 having a suitable shape for the creation of an implant site, as will be described hereunder.

The body 2 of the handpiece is connected to an external connector element 4. The external connector 4 bears electrical supply and hydraulic supply cables designed to be connected respectively to an electrical supply, to a hydraulic supply and to a peristaltic pump provided on a console. The console provides a control panel for operation of the surgical device 1.

Inside the surgical device 1 there is provided a transducer connected to the insert 3. The transducer can be piezoceramic resonator, designed to transform the electrical input signal into a vibration in the ultrasound frequency, so as to make the insert 3 vibrate. For this purpose the transducer is supplied with alternating voltage and current, preferably with a sinusoidal voltage of about 160 Volt r.m.s. at a frequency ranging between 25 kHz and 30 kHz, so as to act as a sound wave concentrator and to set the insert 3 in vibration at an ultrasonic working frequency. An ultrasonic work carrier frequency of 27 kHz is preferably chosen.

According to requirements, the supply signal of the transducer having a carrier ultrasound frequency can be modulated or overmodulated with a low-frequency signal (6-40 Hz); or can be modulated or overmodulated with a series of low-frequency bursts.

The power of the vibrations of the insert 3 is regulated by varying the duty cycle of the signal with the carrier ultrasound frequency and by maintaining constant the duty cycle of the signal at the modulation or overmodulation frequency.

This method, which adopts modulation of the vibration of the insert 3, makes it possible to minimize the heat that develops in the soft tissue because of the energy dissipation due to vibration of the insert.

The method, which provides for use of a carrier signal at ultrasound frequency modulated with low frequency bursts, varying the duty cycle of the carrier signal at ultrasound frequency, makes it possible to have a hammering effect of the insert 3, combined with the efficacy of the ultrasound vibration which causes a clean, precise cut in the mineralized tissues.

As shown in FIGS. 2 and 3, the insert 3 comprises a cylindrical tang 30 designed to be connected to the ultrasonic transducer inside the surgical device 1. The tang 30 comprises a groove 31 designed to be engaged by a mounting key of the handpiece and an inner thread 39 for connection to an attachment of the transducer of the handpiece.

The tang 30 is connected to a shank 32 with a smaller diameter than the tang 30, by means of a tapered transitional portion 33 having a decreasing diameter from the tang 30 to the shank 32.

The shank 32 has at its end a tip 35 which is the working part of the insert 3. The shank 32 has centrally a curved portion 34 so as to be able to direct the tip 35 more easily towards the work area. The curved portion 34 defines an obtuse angle which can range from 90° to 170°.

As shown in FIG. 3, a duct 36 is formed axially in the body of the insert for passage of a cooling fluid, such as a physiological solution for example. The duct 36 is open in the rear part of the tang 30 to be connected to a hydraulic supply tube provided in the handpiece and ends with an outlet duct 37 disposed in the tip 35 of the insert.

From the outlet duct 37 there protrude radially outward a plurality of radial tongues 138, preferably six in number, disposed equidistant from each other by an angle of about 60°. The peripheral edges of the tongues 138 define a circumference having a diameter of about 2-2.5 mm, preferably 2.2 mm.

Each radial tongue 138 comprises a cutting end profile 50 and a cutting lateral profile 51 so as to be able to make an incision in the bone, when the tip 35 of the insert vibrates at ultrasound frequency.

Figure 4:
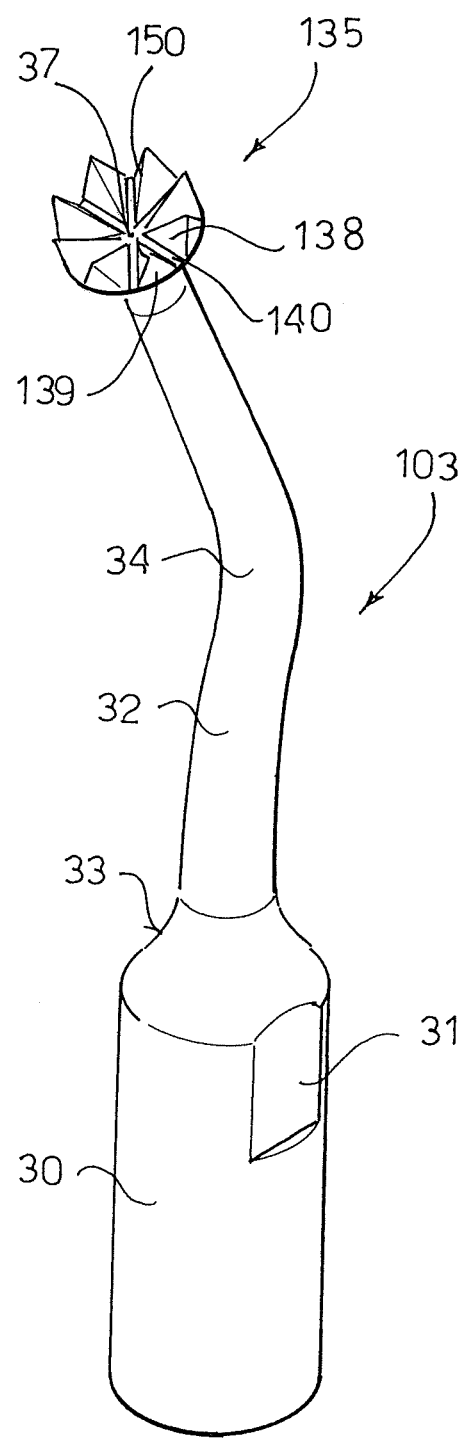
FIG. 4 is a perspective view of a second type of insert.

FIGS. 4 and 5 show a second type of insert 103, in which like or corresponding elements to those already described are denoted with the same reference numerals and are not described in detail.

The insert 103 differs from the insert 3 only in the shape of its tip 135. The tip 135 of the insert 103 has a circular plate 139 at the centre of which the outlet duct 37 opens.

A plurality of segments 138 preferably eight in number, disposed radially with respect to the outlet duct 37 and equidistant from each other by an angle of about 45° are provided on the circular plate 139. Each segment 138 is shaped as a pyramid with an upturned triangular base, with the vertex pointing towards the outlet duct 37. Each segment 138 has a cutting profile 150 which converges radially from the periphery of the segment towards the outlet duct 37.

Corridors 140 which start from the outlet duct 37 and extend radially outward are left between the segments 138.

In this manner the irrigating liquid flows out radially from the outlet duct 37 and spreads radially through the radial corridors 140, so as to maximise the cooling of the cutting area.

The peripheral edges of the segments 138 and of the corridors 140 define a circumference having a diameter of about 2.5-4 mm, preferably 3.3 mm.

In this manner the first insert 3 can be made to form a small diameter hole in the bone and the second insert 103 can be used to enlarge the hole made by the first insert 3.

Performance of the surgical procedure according to the invention is described with reference to FIGS. 6-9.

Figure 6:
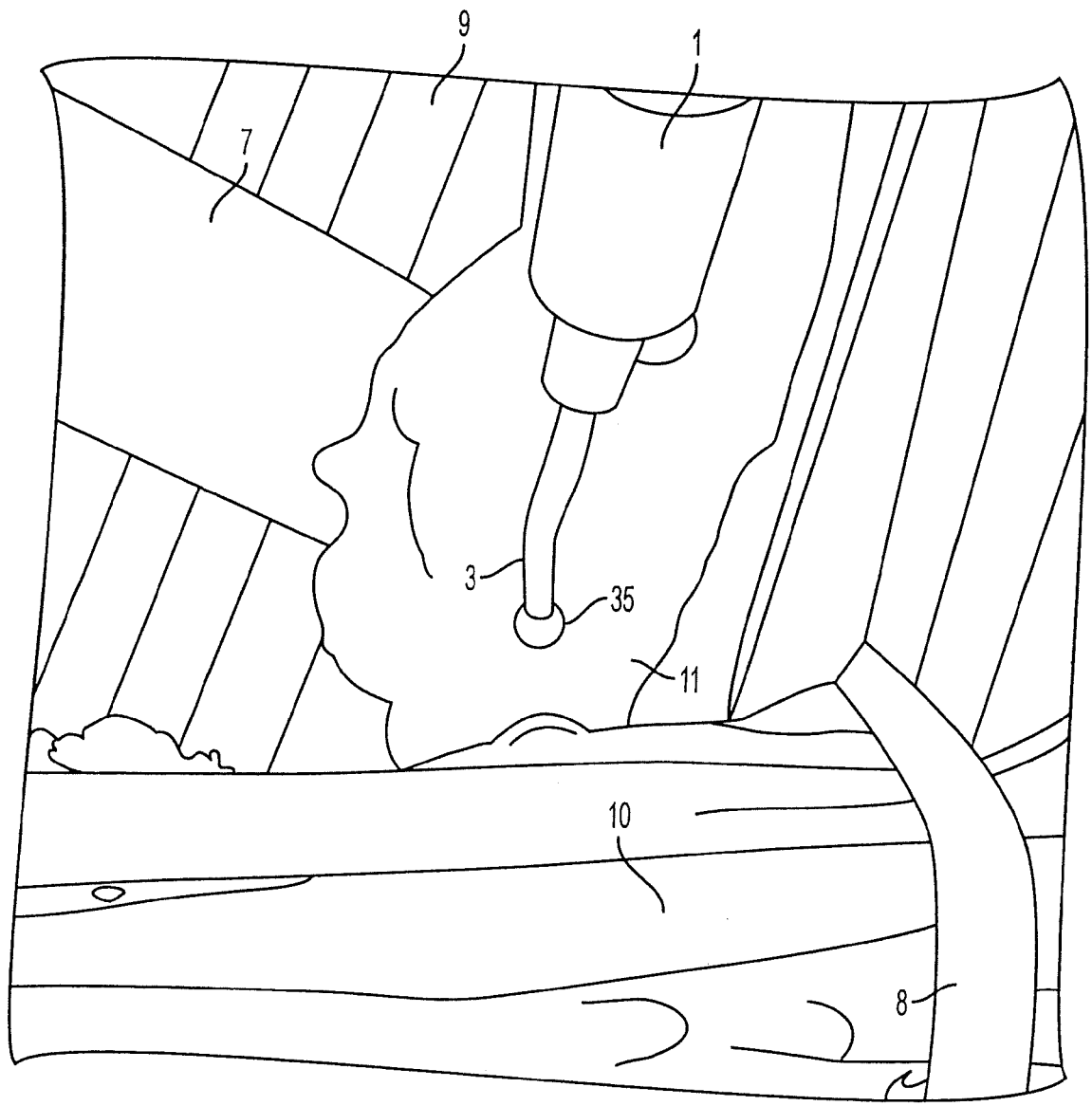
FIGS. 6-9 illustrate the successive steps of the surgical method carried out with the ultrasound handpiece according to the invention.

As shown in FIG. 6, using suitable tools 7, 8 the mucoperiosteal flaps 9 and 10 of the surgical area are lifted so as to expose the bone 11 in which the procedure is to be performed. The smaller diameter tip 35 of the insert 3 of the ultrasound surgical device 1 is applied to the portion of bone 11.

The tip of the insert is made to vibrate at ultrasound frequency and at the same time the cooling fluid passes through the duct 36 inside the insert and reaches the outlet duct 37 in the tip 35 of the insert, from which is flows out, cooling the area on which the tip 35 is working.

A light pressure is exerted with the hand on the surgical device 1, combined with an angular oscillating movement, so that the tip 35 of the insert presses on the bone 11, at the area chosen for the implant site.

Figure 7:
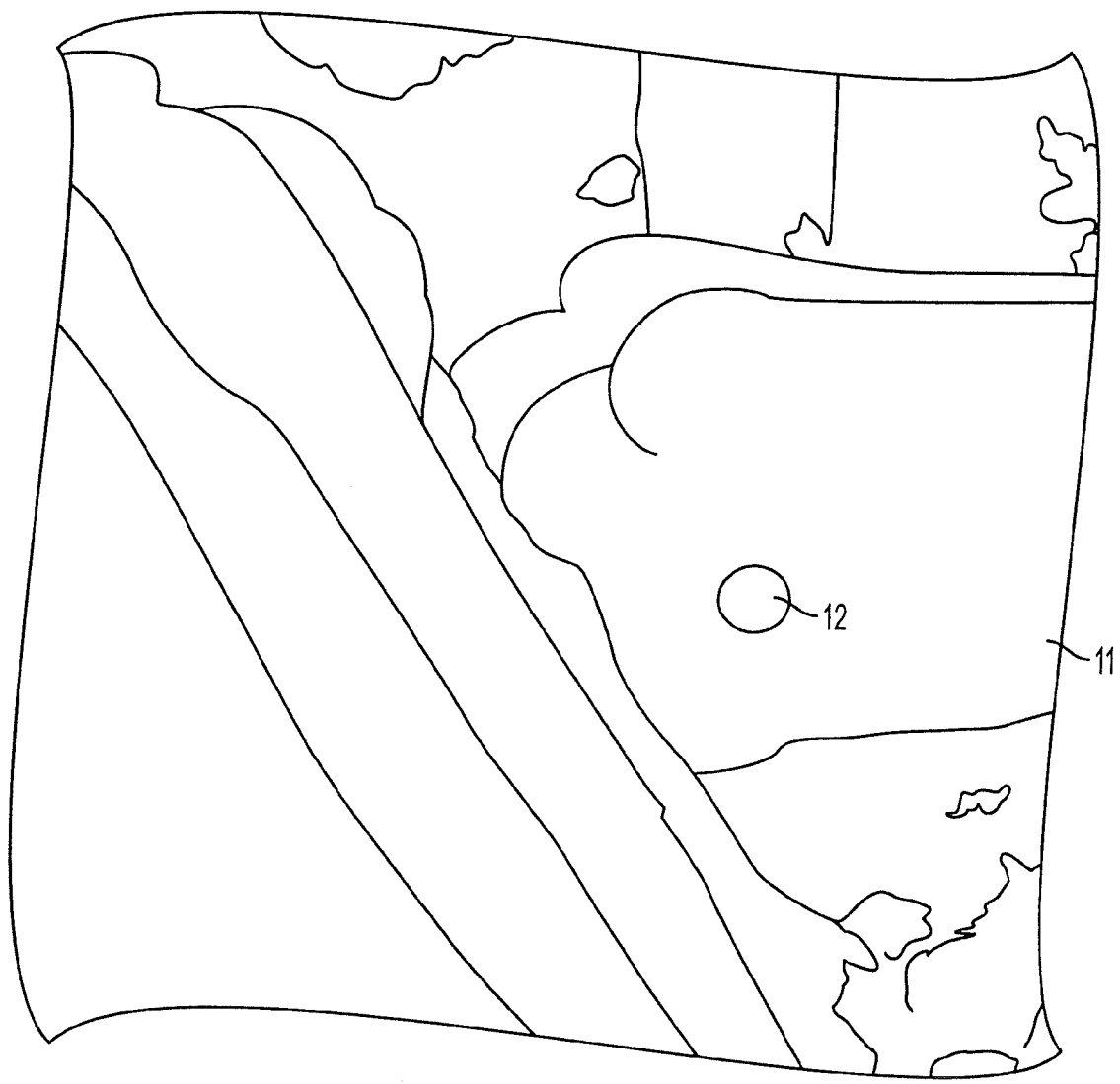

This procedure continues until a suitable depth for the length of the implant is reached. Then the insert 3 is removed from the bone 11 and, as shown in FIG. 7, a hole 12 having a slightly greater diameter than the tip 35 of the insert 3 is left.

Figure 8:
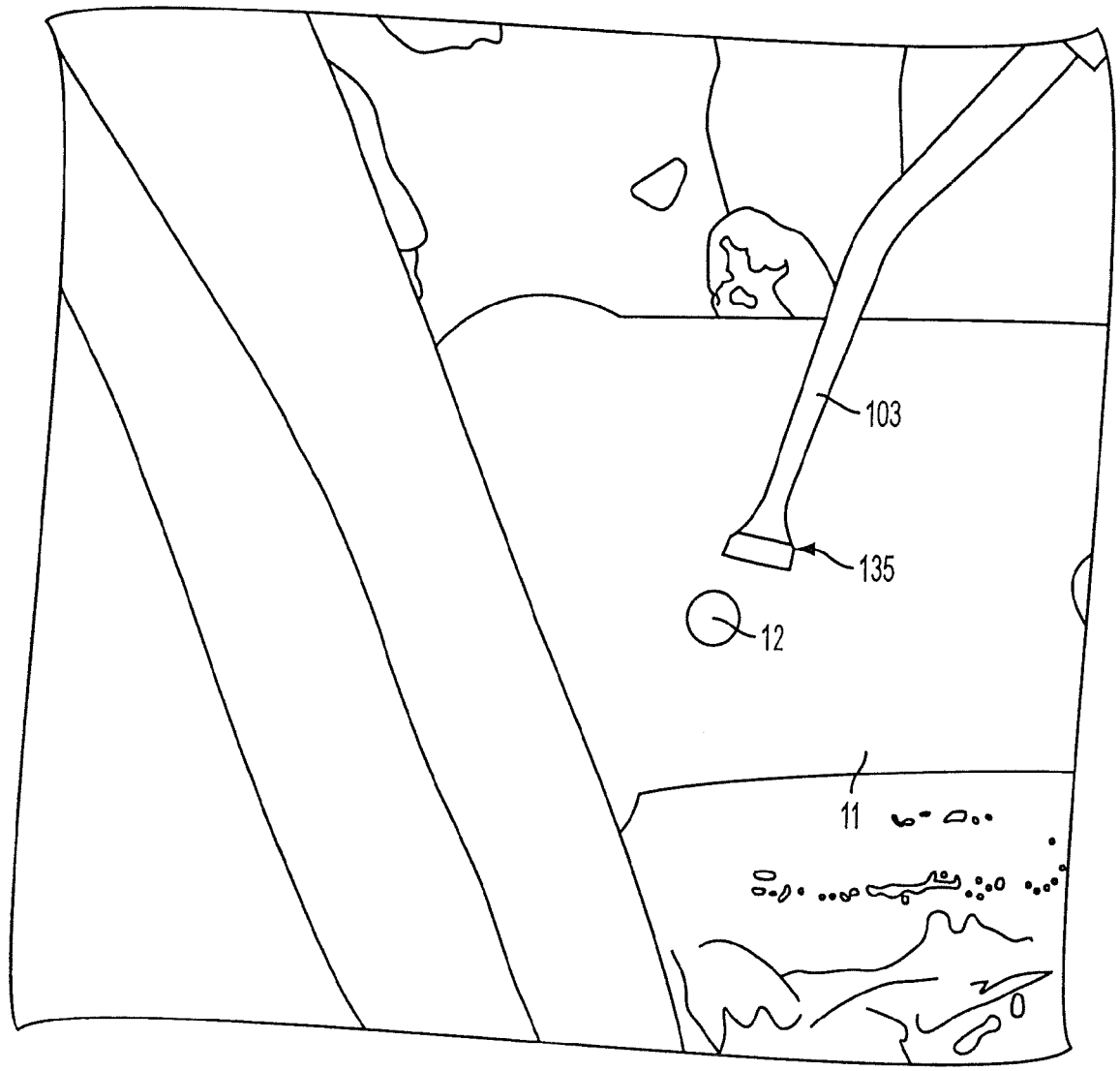
Figure 9:
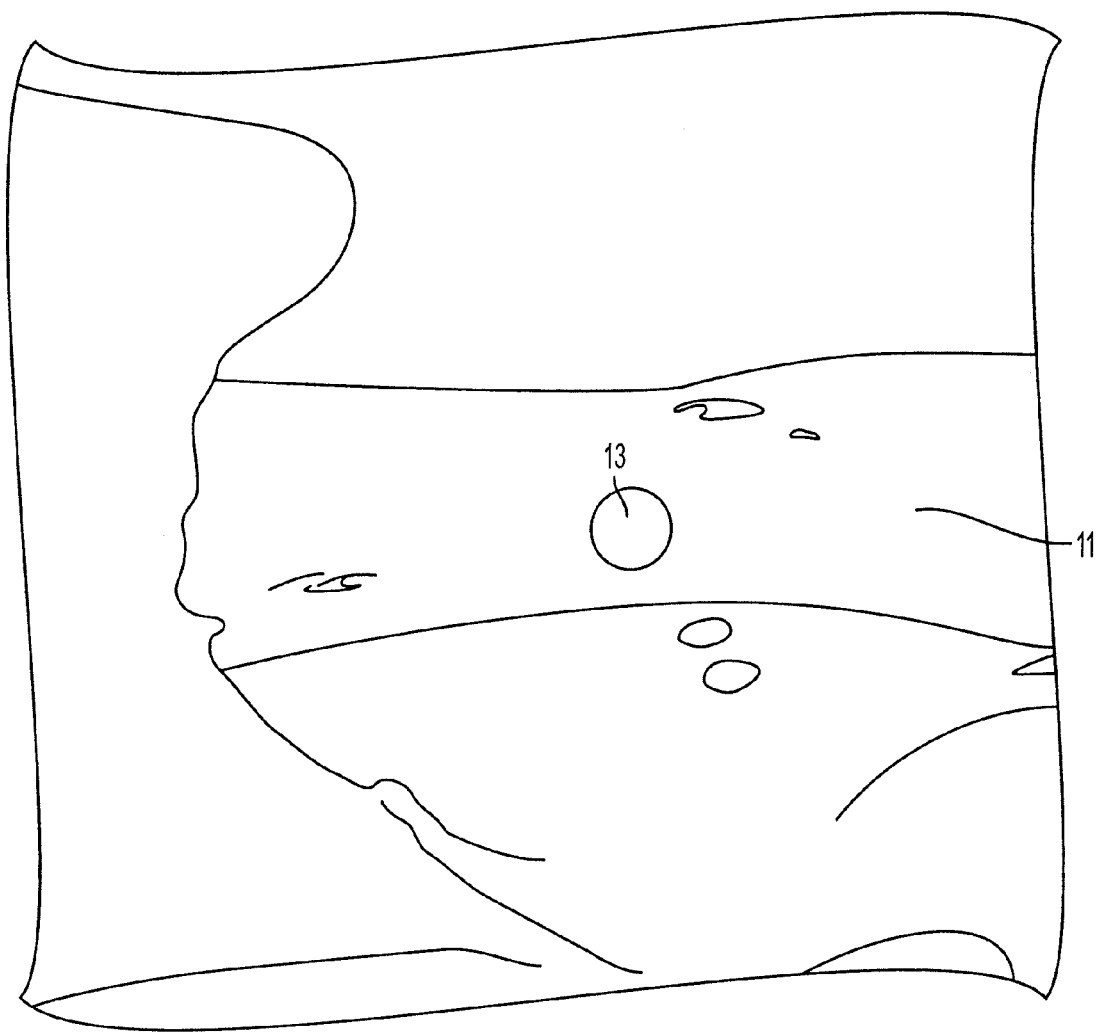

As shown in FIG. 8, at the end of this operation the insert 103 having a tip 135 with a larger diameter is used in a similar fashion so as to enlarge the hole 12, until an enlarged hole 13 (FIG. 9) is obtained, having a diameter substantially equal to the diameter of the selected implant.

At this point the selected implant can be implanted in the hole 13.

This system for the preparation of implant sites holds various advantages.

Extreme ease of execution of the procedure is achieved, thanks to the precision and to the control afforded by ultrasound piezoelectric surgery. The action of traditional devices (micromotors combined with drills) is associated with macrovibrations so that performance of the procedure lacks precision, whereas the action of the ultrasound surgical device 1 is characterized by microvibrations of the insert 3, 103 which allow a greater tactile sensitivity of the operator with a better intraoperative position.

Reliability is achieved in cutting of the bone which, thanks to the particular ultrasonic frequency vibrations of the insert 3, 103, allows a selective cutting, that is a cutting which is effective in removing biological material in mineralized structures (bone) with minimal trauma for the soft tissues and for the delicate structures. Accidental contact of the cutting tip 35, 135 of the insert with a nerve does not cause injury, thus it is possible to operate in safety, even in areas that are anatomically difficult or high risk with traditional instruments.

The duct 36 carries the irrigation fluid to the outlet duct 37 in the tip of the insert, allowing the surgical field to be irrigated precisely, avoiding critical overheating of the bone during the operation.

Use of the surgical device 1 combined with the method described for preparation of the implant site, allows better regeneration of biological tissue compared with traditional methods, as shown by comparative tests on animals reported below with reference to FIGS. 10-14.

Comparative Tests

Sixteen implants (Nobel Biocare porous implants MK III Ti unite) were placed in the tibia of eight minipigs. The experimental animals were divided into two groups of four animals.

In a first group of four animals a single implant per animal was placed and the implant site was prepared using a piezoelectric surgical technique.

In a second group of four animals three implants per animal were placed. In each animal of the second group one implant site was prepared by the piezoelectric surgical method and two implant sites were prepared by a traditional surgical method using Brånemark system drills (control test).

Figure 10:
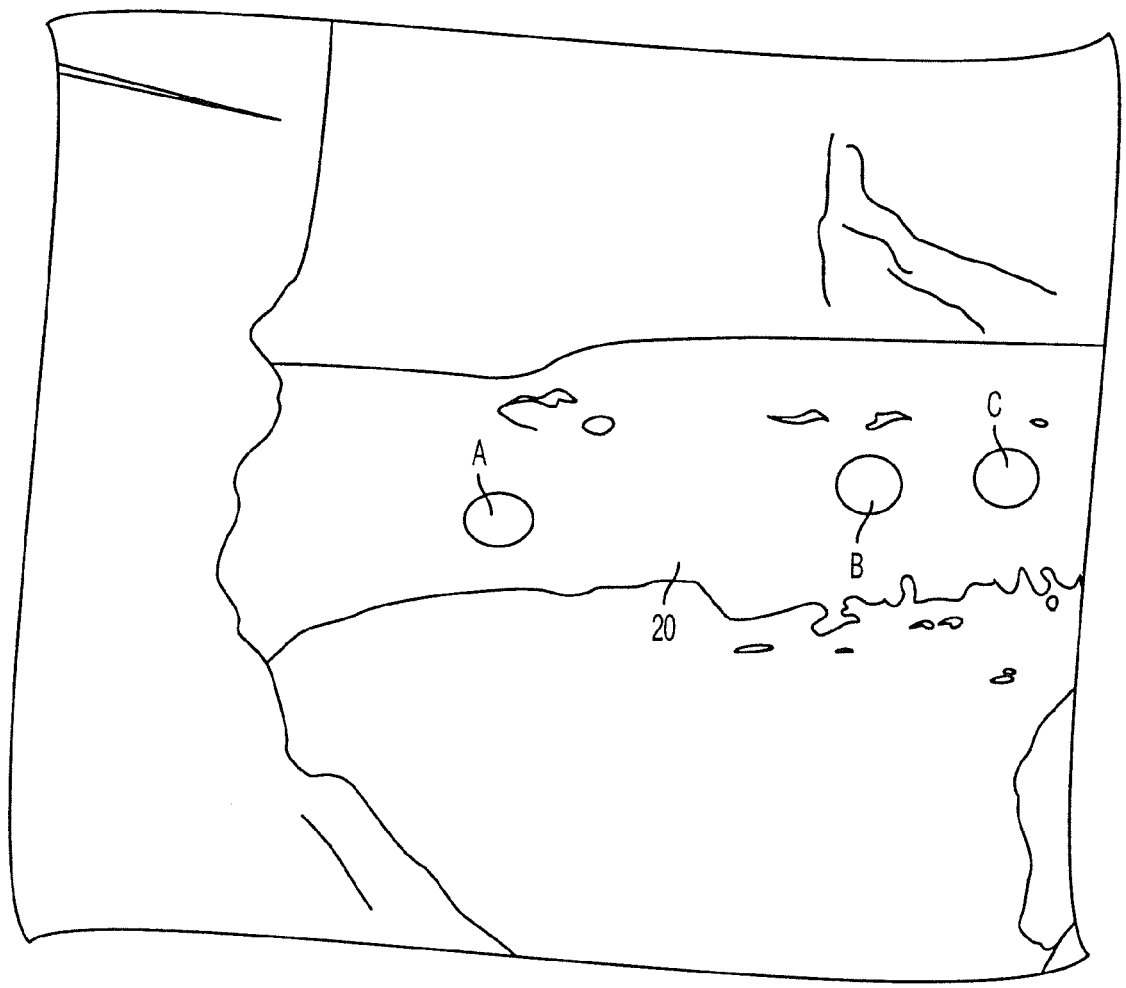
FIG. 10 illustrates an animal bone in which three holes have been made: one with the ultrasound method and the other two with the traditional method.

FIG. 10 shows the bone 20 of the animal in which the hole A was prepared with the piezoelectric method and the holes B and C with the traditional method.

Figure 11:
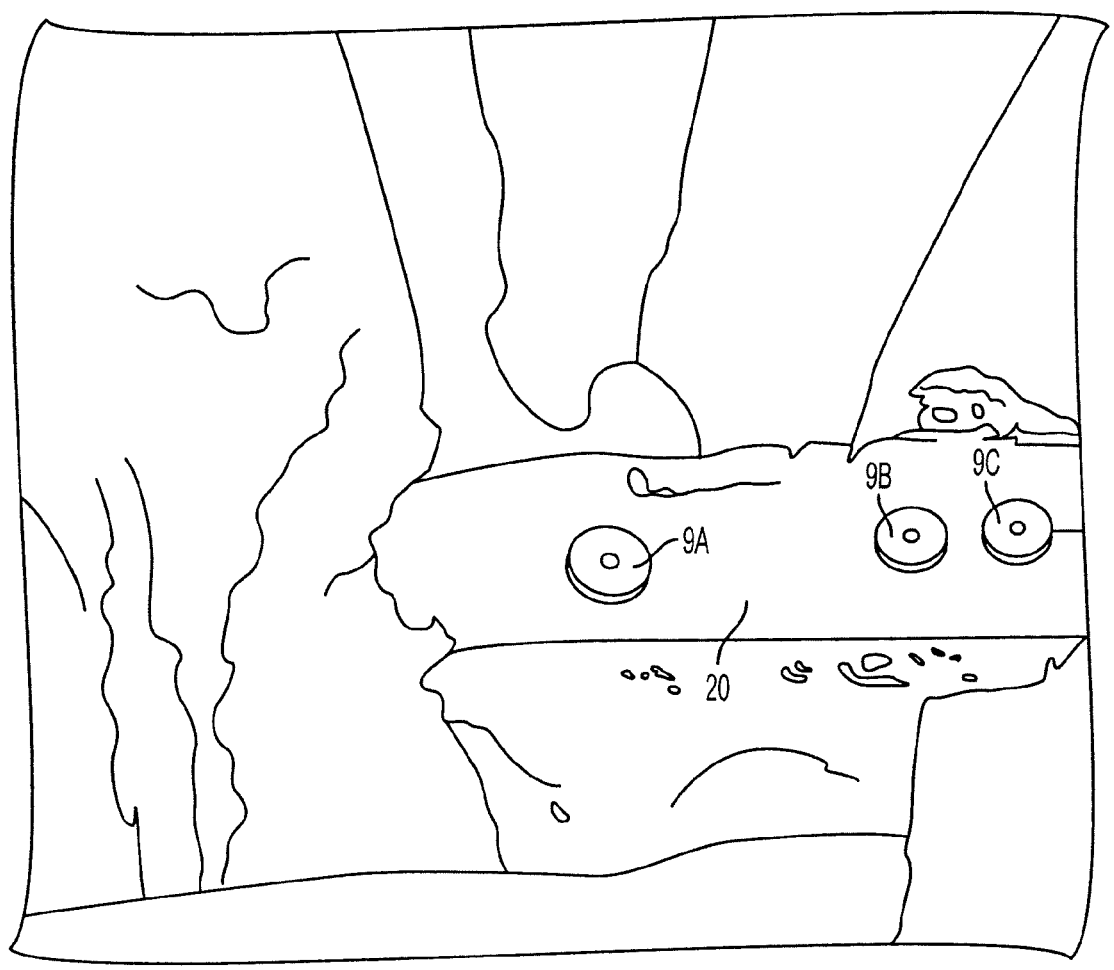
FIG. 11 illustrates the bone of FIG. 10 in which three implants have been implanted in the three holes made previously.

FIG. 11 shows the bone 20 of the animal, in which the implants 9A, 9B and 9C have been implanted in the respective holes A, B and C.

In the second group comprising four animals, each with three implants, the animals were sacrificed at successive intervals of time, namely exactly 7, 14, 28 and 56 days after placement of the implants, to collect the relative autopsy specimens (bone block with implant).

Figure 12:
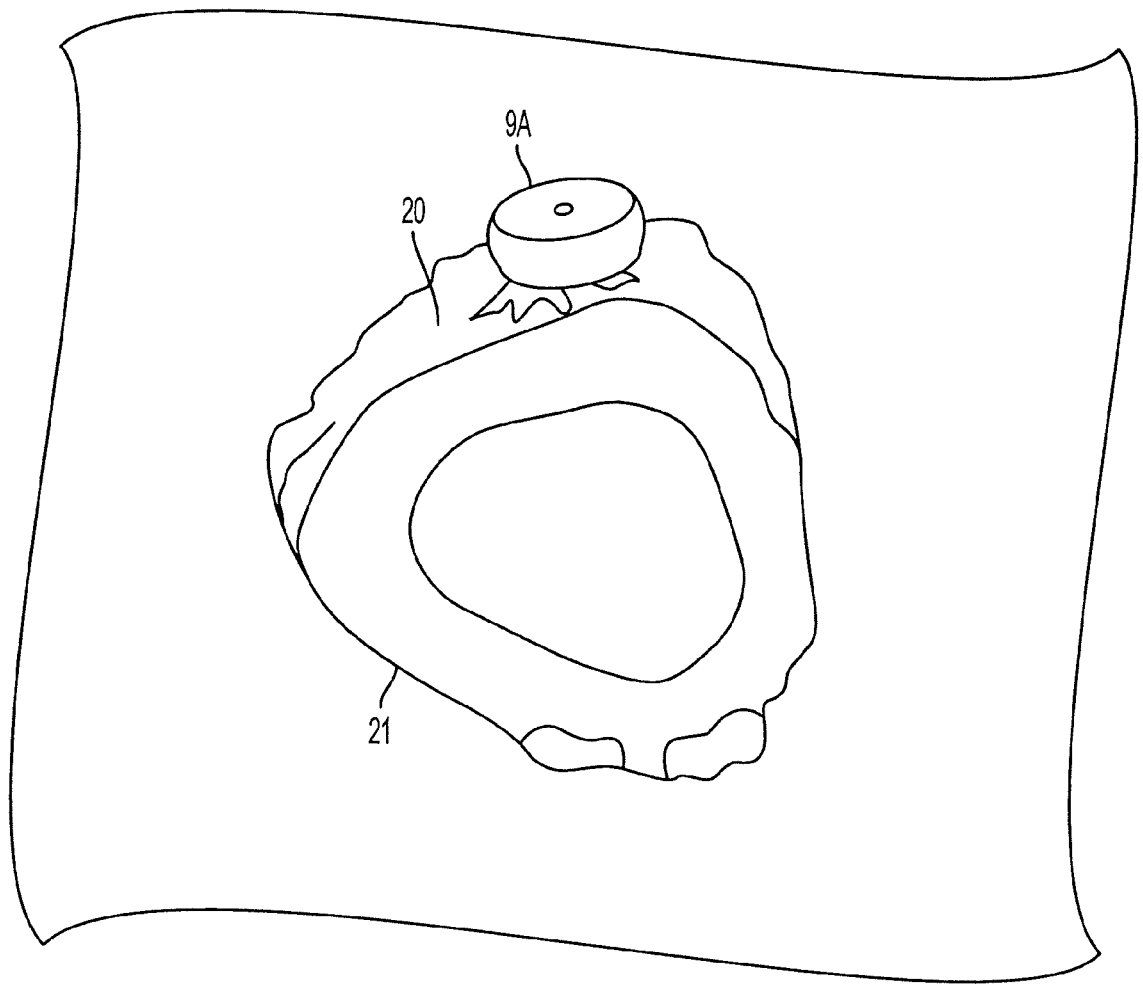
FIG. 12 illustrates an autopsy specimen of the bone of FIG. 11 after a sufficient time for mineralization of the bone around the implant.

FIG. 12 shows an autopsy specimen 21 in which the implant 9A is healed into the bone 20.

The relative autopsy specimens were then subjected to histological (decalcification) and biomolecular tests (cDNA evaluated with PCR Real-Time for gene expression of BMP-4, TGF-β).

Figure 13:
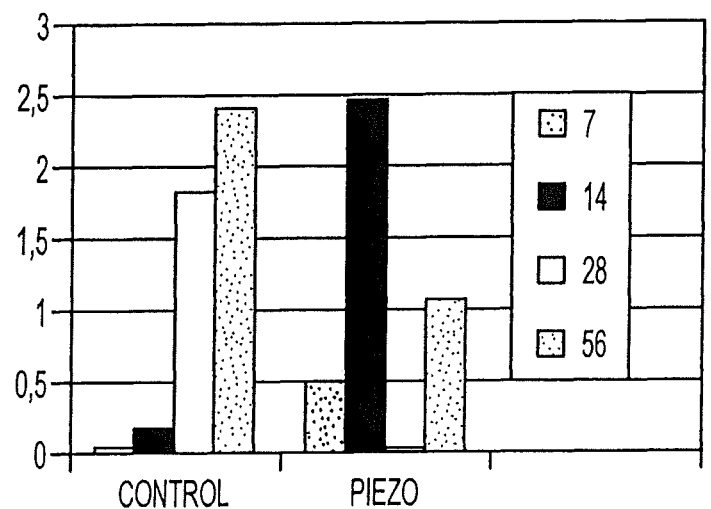
FIGS. 13 and 14 are two histograms showing the results of biomolecular analyses, on the BMP-4 and TGF-β2 molecules respectively, on autopsy specimens collected at successive times on implant sites made with the ultrasound method and with the traditional method.
Figure 14:
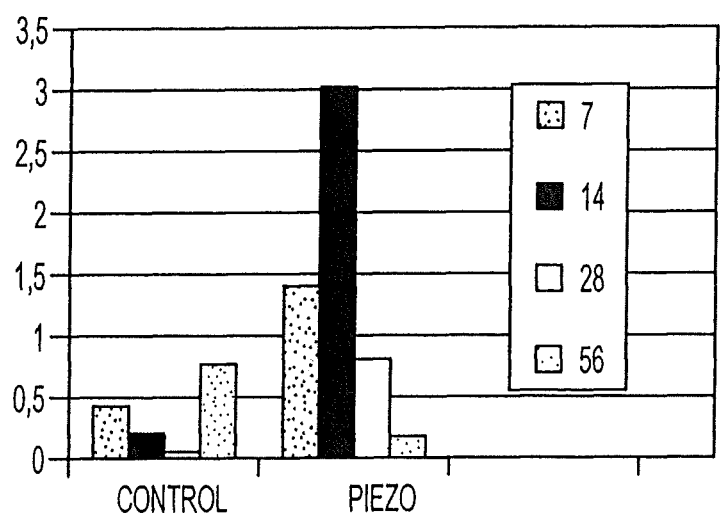

The two surgical methods (traditional and with ultrasound surgical device 1) showed no qualitative histological differences in the times observed. As shown in the graphs of FIGS. 13 and 14, respectively, the biological analysis showed that expression of the two molecules (BMP-4, TGF-β2) was increased in the piezoelectric surgical method (Piezo) in the first experimental times compared with the traditional method (Control).

What is claimed is:

1. A combination of an insert and a handheld ultrasound surgical device, the handheld ultrasound surgical device to provide ultrasound vibrations and fluid to the insert for cutting bone, the insert comprising:
   an interface that receives the ultrasound vibrations from the handheld ultrasound surgical device and provides the fluid from the handheld ultrasound surgical device to a channel within the insert; and
   a tip having a plurality of cutting elements including cutting edges extending from a plurality of periphery edges toward an opening of the channel,
   wherein the plurality of cutting elements is disposed radially from the opening to provide a plurality of radial corridors which start from the opening and extend radially outward for passage of the fluid,
   wherein the plurality of periphery edges forms an exterior circumference of the tip at an end of the tip.

2. The combination of an insert and a handheld ultrasound surgical device of claim 1, wherein the plurality of cutting elements is in the shape of a plurality of radial tongues disposed radially with respect to the opening so that the plurality of peripheral edges of the plurality of radial tongues forms the edge of the tip.

3. The combination of an insert and a handheld ultrasound surgical device of claim 1, wherein each of the plurality of cutting elements is in the form of a pyramid with an upturned triangular base having a vertex pointing toward the opening.

4. The combination of an insert and a handheld ultrasound surgical device of claim 1, further comprising a curved section formed between the interface and the tip, wherein the interface is substantially cylindrical having a first diameter and the curved section is substantially cylindrical having a second diameter that is smaller than the first diameter, wherein the substantially cylindrical curved section is curved away from a longitudinal axis of the interface to the tip.

5. The combination of an insert and a handheld ultrasound surgical device of claim 4, wherein the interface includes an opening to receive a fluid supply tube in the handheld ultrasound surgical device.

6. The combination of an insert and a handheld ultrasound surgical device of claim 5, wherein the interface includes an inner thread surrounding the opening to receive the fluid supply tube, the inner thread to engage the handheld ultrasound surgical device.

7. The combination of an insert and a handheld ultrasound surgical device of claim 1, wherein the ultrasound vibrations received by the interface have a frequency of between approximately 25 KHz and approximately 30 KHz and wherein the ultrasound vibrations received by the interface are modulated with a low frequency signal of between approximately 6 Hz and approximately 40 Hz.

8. The combination of a removable insert and a handheld ultrasound surgical device of claim 1, wherein the ultrasound vibrations received by the interface have a frequency of between approximately 25 KHz and approximately 30 KHz and wherein the ultrasound vibrations received by the interface are modulated with a series of low frequency bursts.

9. A combination of a removable insert and a handheld ultrasound surgical device, the ultrasound handheld surgical device coupled to a power supply to provide an electrical signal and coupled to a pump to provide a fluid, the surgical device to provide the fluid and ultrasound vibrations to the insert in response to the electrical signal, the removable insert comprising:
   an interface that receives the ultrasound vibrations from the handheld ultrasound surgical device and provides the fluid from the handheld ultrasound surgical device to a channel within the insert; and
   a tip having an end including a plurality of cutting elements, each cutting element has a periphery edge surface that forms an approximate exterior circumference of the tip at the end of the tip,
   wherein each of the cutting elements includes a cutting profile having a cutting edge that extends radially from each of the periphery edge surfaces and each cutting edge converges at an opening of the channel that is at an approximate center of the tip.

10. The combination of a removable insert and a handheld ultrasound surgical device of claim 9, wherein the plurality of cutting elements is in the shape of a plurality of radial tongues disposed radially with respect to the opening.

11. The combination of a removable insert and a handheld ultrasound surgical device of claim 9, wherein each of the plurality of cutting elements is in the form of a pyramid.

12. The combination of a removable insert and a handheld ultrasound surgical device of claim 9, wherein the interface includes an opening to receive the fluid from the handheld ultrasound surgical device.

13. The combination of a removable insert and a handheld ultrasound surgical device of claim 12, wherein the interface includes an inner thread surrounding the opening to receive the fluid from the handheld ultrasound surgical device, the inner thread to engage the insert to the handheld ultrasound surgical device.

14. The combination of a removable insert and a handheld ultrasound surgical device of claim 13, wherein the plurality of cutting elements forms a plurality of corridors for the fluid to flow from the opening in the tip to an edge of the tip.

15. A combination of an insert and a handheld ultrasound surgical device that provides fluid and ultrasound vibrations to the insert, the insert comprising:
    an interface that receives the ultrasound vibrations from the handheld ultrasound surgical device and provides the fluid from the handheld ultrasound surgical device to a channel within the insert, the interface includes an opening to receive the fluid from the handheld ultrasound surgical device; and
    a tip that includes a circular plate at a proximal end of the tip forming an opening at an approximate center, the circular plate disposes a plurality of cutting elements,
    wherein each of the cutting elements are disposed radially from the opening to provide a plurality of linear corridors between respective cutting elements to allow for the passage of the fluid from the opening to an edge of the circular plate,
    wherein the plurality of cutting elements includes a plurality of periphery edges that forms an exterior circumference of the tip at a distal end of the tip.

16. The combination of an insert and a handheld ultrasound surgical device of claim 15, wherein the plurality of cutting elements is disposed in a substantially circular configuration around the opening.

17. The combination of an insert and a handheld ultrasound surgical device of claim 16, wherein each of the plurality of cutting elements is in the shape of a plurality of radial tongues disposed radially with respect to the opening in the tip.

18. The combination of an insert and a handheld ultrasound surgical device of claim 16, wherein each of the plurality of cutting elements is in the form of a pyramid.

* * * * *